US008998836B2

(12) United States Patent
Chapman et al.

(10) Patent No.: US 8,998,836 B2
(45) Date of Patent: *Apr. 7, 2015

(54) NOISE-REDUCING DIALYSIS SYSTEMS AND METHODS OF REDUCING NOISE IN DIALYSIS SYSTEMS

(71) Applicants: Baxter International Inc., Deerfield, IL (US); Baxter Healthcare S.A., Glattpark (Opfikon) (CH)

(72) Inventors: Paul R. Chapman, Lutz, FL (US); Robert W. Childers, Trinity, FL (US); Gideon Hecht, Seminole, FL (US); Anders Wellings, Largo, FL (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/919,308

(22) Filed: Jun. 17, 2013

(65) Prior Publication Data

US 2013/0277306 A1  Oct. 24, 2013

Related U.S. Application Data

(60) Continuation of application No. 13/047,203, filed on Mar. 14, 2011, now Pat. No. 8,465,446, which is a division of application No. 11/929,330, filed on Oct. 30, 2007, now Pat. No. 7,905,853.

(51) Int. Cl.
*A61M 1/14* (2006.01)
*A61M 1/00* (2006.01)
(Continued)

(52) U.S. Cl.
CPC .............. *A61M 1/14* (2013.01); *F15B 13/0825* (2013.01); *F15B 13/0807* (2013.01);
(Continued)

(58) Field of Classification Search
CPC ................ A61M 2205/42; A61M 2205/43; A61M 1/14; A61M 1/28; A61M 1/281; A61M 2205/128; A61M 2205/12; A61M 1/1037; A61M 1/1087; A61M 1/1096; A61M 1/1649; A61M 1/30; B01J 2219/00396; B01J 2219/00398; F15B 1/021; F15B 21/008; F15B 21/006
USPC ............................ 604/4.01, 6.1, 6.11; 422/44
See application file for complete search history.

(56) References Cited

U.S. PATENT DOCUMENTS 2,823,724 A  2/1958 Davis
3,565,873 A  2/1971 Schiff
(Continued)

FOREIGN PATENT DOCUMENTS

| EP | 0085016 | 8/1983 |
|---|---|---|
| EP | 0097432 | 1/1984 |
| EP | 0157024 | 9/1985 |
| EP | 0204260 | 12/1986 |
| EP | 0206195 | 12/1986 |
| EP | 0248632 | 12/1987 |
| EP | 0402505 | 12/1990 |
| EP | 0459647 | 12/1990 |

(Continued)

OTHER PUBLICATIONS

Search Report and Written Opinion for corresponding International Application No. PCT/US2008/081315 completed on Mar. 25, 2009.

*Primary Examiner* — Adam Marcetich
(74) *Attorney, Agent, or Firm* — K&L Gates LLP

(57) ABSTRACT

A method of pneumatically operating a dialysis system includes (i) pumping air in a first valve state from a pneumatic pump to operate a component of the dialysis system, and (ii) recirculating air in a second valve state by pumping air from an outlet of the pneumatic pump to an inlet of the pneumatic pump to minimize at least one of a noise pitch or noise amplitude when switching from the second valve state to the first valve state.

11 Claims, 13 Drawing Sheets

(51) Int. Cl.
    *B01D 61/24* (2006.01)
    *B01D 61/28* (2006.01)
    *B01D 61/30* (2006.01)
    *A61M 1/30* (2006.01)
    *A61M 1/16* (2006.01)
    *A61M 1/10* (2006.01)
    *A61M 1/28* (2006.01)
    *F15B 13/08* (2006.01)
    *F16K 99/00* (2006.01)
    *F15B 21/00* (2006.01)
    *F15B 1/02* (2006.01)

(52) U.S. Cl.
    CPC .............. B01J 2219/00396 (2013.01); F16K 2099/0082 (2013.01); B01J 2219/00412 (2013.01); F15B 13/0832 (2013.01); F15B 13/0835 (2013.01); B01J 2219/00398 (2013.01); F16K 99/0042 (2013.01); F15B 13/0842 (2013.01); B01J 2219/00409 (2013.01); F15B 13/0817 (2013.01); F15B 13/0814 (2013.01); F16K 2099/0086 (2013.01); F15B 13/0828 (2013.01); F15B 13/0821 (2013.01); F15B 21/006 (2013.01); A61M 2205/42 (2013.01); A61M 2205/12 (2013.01); *A61M 1/30* (2013.01); F15B 1/021 (2013.01); *A61M 1/1649* (2013.01); *A61M 1/1037* (2013.01); *A61M 1/1087* (2013.01); F15B 21/008 (2013.01); *A61M 1/28* (2013.01); A61M 2205/128 (2013.01); *A61M 1/281* (2013.01)

(56) References Cited

U.S. PATENT DOCUMENTS

| | | |
|---|---|---|
| 3,656,873 A | 4/1972 | Schiff |
| 3,689,204 A | 9/1972 | Prisk |
| 3,709,222 A | 1/1973 | DeVries |
| 3,783,453 A | 1/1974 | Bolie |
| 3,823,724 A | 7/1974 | Davis |
| 3,841,093 A | 10/1974 | Smith |
| 3,882,899 A | 5/1975 | Ginsberg et al. |
| 3,919,722 A | 11/1975 | Harmison |
| D240,559 S | 7/1976 | Kawaguchi |
| 4,086,653 A | 4/1978 | Gernes |
| 4,158,530 A | 6/1979 | Bernstein |
| 4,162,543 A | 7/1979 | Shumakov et al. |
| 4,175,264 A | 11/1979 | Schiff |
| 4,199,307 A | 4/1980 | Jassawalla |
| 4,236,880 A | 12/1980 | Archibald |
| 4,240,408 A | 12/1980 | Schael |
| 4,257,746 A | 3/1981 | Wells |
| 4,265,601 A | 5/1981 | Mandroian |
| 4,273,121 A | 6/1981 | Jassawalla |
| 4,277,226 A | 7/1981 | Archibald |
| 4,373,527 A | 2/1983 | Fischell |
| 4,381,003 A | 4/1983 | Buoncristiani |
| 4,381,567 A | 5/1983 | Robinson et al. |
| 4,413,988 A | 11/1983 | Handt et al. |
| D271,801 S | 12/1983 | Preussner |
| D271,802 S | 12/1983 | Preussner |
| 4,435,719 A | 3/1984 | Snaper |
| 4,467,844 A | 8/1984 | Di Gianfilippo et al. |
| 4,468,222 A | 8/1984 | Lundquist |
| 4,479,760 A | 10/1984 | Bilstad et al. |
| 4,479,761 A | 10/1984 | Bilstad |
| 4,479,762 A | 10/1984 | Bilstad |
| 4,552,552 A | 11/1985 | Polaschegg et al. |
| 4,559,036 A | 12/1985 | Wunsch |
| 4,613,327 A | 9/1986 | Tegrarian et al. |
| 4,634,430 A | 1/1987 | Polaschegg |
| 4,657,529 A | 4/1987 | Prince et al. |
| 4,662,358 A | 5/1987 | Farrar et al. |
| 4,670,007 A | 6/1987 | Wheeldon et al. |
| 4,778,451 A | 10/1988 | Kamen |
| 4,808,161 A | 2/1989 | Kamen |
| 4,816,019 A | 3/1989 | Kamen |
| 4,818,186 A | 4/1989 | Pastrone et al. |
| 4,826,482 A | 5/1989 | Kamen |
| 4,828,545 A | 5/1989 | Epstein et al. |
| 4,865,584 A | 9/1989 | Epstein et al. |
| 4,925,152 A | 5/1990 | Huber |
| 4,927,411 A | 5/1990 | Pastrone et al. |
| 4,976,162 A | 12/1990 | Kamen |
| 5,000,664 A | 3/1991 | Lawless et al. |
| 5,062,774 A | 11/1991 | Kramer et al. |
| 5,088,515 A | 2/1992 | Kamen |
| 5,108,367 A | 4/1992 | Epstein et al. |
| 5,112,298 A | 5/1992 | Prince et al. |
| 5,141,492 A | 8/1992 | Dadson et al. |
| 5,141,493 A | 8/1992 | Jacobsen et al. |
| 5,149,413 A | 9/1992 | Maget |
| 5,178,182 A | 1/1993 | Kamen |
| 5,193,990 A | 3/1993 | Kamen et al. |
| 5,200,090 A | 4/1993 | Ford et al. |
| 5,205,819 A | 4/1993 | Ross et al. |
| H001326 H | 7/1994 | Lefebvre |
| 5,344,292 A | 9/1994 | Rabenau et al. |
| 5,350,357 A | 9/1994 | Kamen et al. |
| 5,380,267 A * | 1/1995 | Boutelle et al. .................. 600/18 |
| 5,431,626 A | 7/1995 | Bryant et al. |
| 5,437,624 A | 8/1995 | Langley |
| 5,438,510 A | 8/1995 | Bryant et al. |
| 5,445,506 A | 8/1995 | Afflerbaugh et al. |
| 5,460,493 A | 10/1995 | Deniega et al. |
| 5,484,239 A | 1/1996 | Chapman et al. |
| 5,520,333 A | 5/1996 | Tofte |
| 5,593,290 A | 1/1997 | Greisch et al. |
| 5,628,908 A | 5/1997 | Kamen et al. |
| 5,651,766 A | 7/1997 | Kingsley et al. |
| 5,676,644 A | 10/1997 | Toavs et al. |
| 5,816,779 A | 10/1998 | Lawless et al. |
| 5,938,634 A | 8/1999 | Packard |
| 6,069,792 A | 5/2000 | Nelik |
| 6,416,293 B1 | 7/2002 | Bouchard et al. |
| 6,481,980 B1 | 11/2002 | Vandlik et al. |
| 6,485,263 B1 | 11/2002 | Bryant et al. |
| 6,497,676 B1 | 12/2002 | Childers et al. |
| 6,604,908 B1 | 8/2003 | Bryant et al. |
| 6,638,478 B1 | 10/2003 | Treu et al. |
| 6,749,403 B2 | 6/2004 | Bryant et al. |
| 6,759,007 B1 | 7/2004 | Westberg et al. |
| 7,087,036 B2 | 8/2006 | Busby et al. |
| 7,195,607 B2 | 3/2007 | Westberg et al. |
| 7,238,164 B2 | 7/2007 | Childers et al. |
| 7,744,554 B2 | 6/2010 | Howard |
| 2003/0072652 A1 | 4/2003 | Danby |
| 2003/0155371 A1 | 8/2003 | Collasius et al. |
| 2003/0220598 A1 | 11/2003 | Busby et al. |
| 2004/0118115 A1 | 6/2004 | Bird et al. |
| 2006/0051218 A1 | 3/2006 | Harttig |
| 2007/0043976 A1 | 2/2007 | Cunningham et al. |
| 2007/0112297 A1 | 5/2007 | Plahey et al. |
| 2007/0131883 A1 | 6/2007 | Goodrich et al. |
| 2008/0033346 A1 | 2/2008 | Childers et al. |
| 2008/0138223 A1 | 6/2008 | Lanigan et al. |
| 2008/0196720 A1 * | 8/2008 | Kollmeyer et al. ...... 128/204.21 |
| 2008/0240951 A1 | 10/2008 | Domash et al. |
| 2008/0243211 A1 * | 10/2008 | Cartwright et al. ............. 607/63 |
| 2009/0016915 A1 | 1/2009 | Caramuta |
| 2009/0025564 A1 * | 1/2009 | Kuwabara ...................... 96/388 |
| 2009/0077957 A1 | 3/2009 | Noble et al. |

FOREIGN PATENT DOCUMENTS

| | | |
|---|---|---|
| EP | 0491159 | 6/1992 |
| GB | 2093800 | 10/1981 |
| WO | 86/01115 | 2/1986 |
| WO | 90/13795 | 11/1990 |
| WO | 94/20158 | 9/1994 |
| WO | 2004/060449 | 7/2004 |

* cited by examiner

NOISE-REDUCING DIALYSIS SYSTEMS AND METHODS OF REDUCING NOISE IN DIALYSIS SYSTEMS

PRIORITY

This application claims priority to and the benefit as a continuation application of U.S. patent application Ser. No. 13/047,203, filed Mar. 14, 2011, entitled, "Noise Reducing Dialysis Systems and Methods of Reducing Noise in Dialysis Systems", which claims priority to and the benefit as a divisional application of U.S. patent application Ser. No. 11/929,330, filed Oct. 30, 2007, entitled, "Dialysis System Having Integrated Pneumatic Manifold", now U.S. Pat. No. 7,905,853, the entire contents of each of which are incorporated herein by reference and relied upon.

BACKGROUND

The present disclosure relates generally to a medical fluid delivery system and in particular to a dialysis system. U.S. Patent No. 5,350,357, the entire contents of which are incorporated herein by reference, shows a peritoneal dialysis machine 10 having housing 12. Housing 12 holds a bag heater module 14 located under a bag heating plate 16. Housing 12 further encloses a pneumatic actuator module 20. Pneumatic actuator module 20 incorporates a cassette holder 22 that holds a disposable dialysis cassette (not illustrated) and a liquid shutoff assembly 24. Machine housing 12 further encloses a source 30 of pneumatic pressure and an associated pneumatic pressure distribution module 40, which links the pressure source 30 with the actuator module 20. Pressure distribution module 40 stores positive pressure in reservoir 32 and negative pressure in reservoir 34. Machine housing 12 also encloses an AC power supply module 36 and a back-up DC battery power supply module 38 to power machine 10.

Tubing 42 connects pneumatic valves located on pressure distribution module 40 to the machine components that operate using pneumatic pressure. Slots 44 in the side of the pressure distribution module 40 accommodate the passage of the tubing 42. In particular, tubing 42 runs from pressure distribution module 40 to actuator module 20, where the tubing connects to components such as a cassette sealing bladder (not illustrated), an occluder bladder for liquid shutoff assembly 24 and to pump and valve actuators that control the application of positive and negative pressure to different areas of the disposable cassette.

Each of the tubes 42 has to be disconnected individually to remove either pressure distribution module 40 to actuator module 20 from machine 10. Tubes 42 are not easy to disconnect. Tubing 42 often stretches and becomes unusable when pulled off the barbed fittings connected to pressure distribution module 40. The barbed fittings themselves can be damaged if an attempt is made to cut tubes 42 off the fittings.

FIG. 2 shows pressure distribution module 40 exploded. Pressure distribution module 40 includes a printed circuit board 46 which is carried on stand-off pins 48 atop the pressure distribution module. Pressure transducers 50 mounted on printed circuit board 46 of module 40 sense through associated sensing tubes 52 pneumatic pressure conditions present at various points along the air conduction channels (not illustrated) within pressure distribution module 40. Pressure transducers 50 and/or the solder joint that connect the pressure transducers to the printed circuit board 46 can be damaged if an attempt is made to disconnect the tubes between the manifold and the pressure transducers.

Attempts to detach the tubing from actuator module 20 also encounter problems. FIG. 3 shows a cassette interface 26, which is located inside actuator module 20. T-fittings 28 connect the tubing 42 to the ports of the valve actuators and pump actuators. Thus to remove actuator module 20 from pressure distribution module 40, cassette interface 26 has to be accessed first and then T-fittings 28 have to be removed from cassette interface 26.

A need therefore exists for a dialysis machine that is more readily repaired and maintained.

SUMMARY

The present disclosure relates to an integrated pneumatic manifold with direct mounted or encapsulated parts that eliminate the need for certain tubes or hoses. The manifold can be used in medical fluid delivery treatments, such as any type of dialysis treatment or machine, e.g., one operating on pneumatic pressure. The manifold can incorporate other pneumatic components besides valves, such as one or more storage reservoir, a pressure pump and a manual diverter valve for calibration standard connection.

The manifold in one embodiment includes a printed circuit board ("PCB") with pneumatic valve drives. The manifold also has easily removable port headers with multiple tubing connections for tubes leading to other subsystems. Valves attached to the PCB communicate with the ports of the header via pneumatic traces or grooves formed in the plate to which the PCB and headers are mounted. The PCB containing the valve drivers also includes a spike and hold circuit in one embodiment that minimizes the holding current required when the valves remain energized for more than a certain period of time, e.g., about 0.1 seconds.

The air pump is mounted in one embodiment to a lower manifold plate, which serves as a heat sink for the air pump motor. The lower plate can therefore be made of a light, thermally conductive material, such as aluminum. The lower plate attaches to the upper plate holding the PCB, valves and headers via a gasket between the plates. The gasket seals the pneumatic pathways or grooves formed on the underside of the upper plate.

The port headers allow the manifold assembly to be detached easily from the dialysis machine, e.g., from a door assembly and electronics in the machine to which the ports and PCB are connected respectively. Any of the manifold subassembly, door subassembly or control board subassembly can be removed and replaced without having to (i) replace any of the interconnecting tubing or (ii) remove any other machine subassembly. The potential to damage any of the interconnecting components is accordingly minimized. For example, tubing does not have to be detached from barbed ports fittings, which otherwise can potentially damage the fitting in addition to destroying the tubing.

A filter that prevents particles from entering the manifold is also integrated into the manifold. In a one embodiment, the filter is a flat filter element that is sandwiched between the upper and lower plates of the manifold. As mentioned, pneumatic reservoirs (shown above as stand-alone positive and negative pressure source tanks 32 and 34) are also integrated into the manifold in one embodiment. Many of the header ports to the valves connect directly into the reservoirs. Pressure transducers can also connect directly into the reservoirs and are thereby uneffected by the transient dynamic conditions that occur in the pneumatic tubing when the system is operating. The manual diverter valve connected to the assembly allows an external pressure standard to be connected to the manifold during calibration to calibrate the pressure transducers.

The manifold assembly works in a pneumatic system to operate a medical fluid system such as a dialysis system. The manifold, for example, can deliver positive or negative air to dialysis fluid pump and valve actuators. The actuators actuate pump and valve chambers located on a disposable fluid cassette. The cassette needs to be sealed to a cassette interface (e.g., shown above as interface 26). In one embodiment therefore the manifold assembly also provides pressure to a bladder that presses the cassette against the cassette interface for operation. Tubes connected to the cassette receive dialysis fluid, carry fresh dialysis fluid to the patient, and carry spent dialysis fluid from the patient to drain. When the machine is not in use or in the event that the machine loses power, the tubes are crimped closed via a spring-loaded occluder that crimps the tubing unless otherwise acted upon. In one embodiment, the manifold assembly pressurizes a second bladder, which operates to retract the occluder to uncrimp or open the tubing.

In the pneumatic system of the present disclosure, the air pump pressurizes four separate tanks, namely, the positive and negative reservoirs located on the manifold assembly, the cassette sealing bladder and the occluder bladder. The pneumatic configurations shown below include apparatuses that allow the air pump to pressurize each of the tanks and bladders individually so that one does not "steal" pressure or air from another during operation of the machine. For example, the air pump located on the manifold assembly in one embodiment includes dual pump heads, which can be dedicated to pumping positive and negative pressure, respectively, to the positive and negative reservoirs. Indeed, the pump can pump to the positive and negative reservoirs simultaneously. This has been found to have the added benefit of halving the pump output to each reservoir, reducing noise.

The pneumatic system isolates the reservoirs from the bladders and the bladders from each other using valves. To conserve the number of valves, the system in one embodiment uses a three-way valve to supply pressurized air to either a positive pressure tank for operating the fluid pumps or to a line that supplies a cassette sealing bladder and a tubing pumping occluder bladder. Also, to conserve the number of solenoid valves needed, the system in one embodiment places a check valve in a split in a line that supplies pressure to the cassette sealing bladder and occluder bladders, such that the occluder bladder cannot steal positive pressure from the cassette sealing bladder. A drop in the cassette sealing bladder pressure can compromise the seal of the dialysis pumping cassette relative to the dialysis instrument.

It is accordingly an advantage of the present disclosure to provide a pneumatic manifold assembly having improved reliability, ease of assembly and serviceability while being backwards compatible with existing systems.

It is another advantage of the present disclosure to provide a pneumatic manifold assembly that integrates the air pump, heat sinks the air pump and places the air pump inside a sealed enclosure to minimize the noise without overheating the pump and valves.

It is a further advantage of the present disclosure to mitigate dialysis instrument noise.

It is still another advantage of the present disclosure to provide a valve manifold assembly configured to isolate two separate sealing bladders pressurized via the manifold assembly.

It is yet a further advantage of the present disclosure to provide a robust pneumatic system in which pneumatic storage tanks and bladders are pneumatically isolated form one another.

Additional features and advantages are described herein, and will be apparent from, the following Detailed Description and the figures.

DETAILED DESCRIPTION

Pneumatic Hardware Configurations

Figure 1:
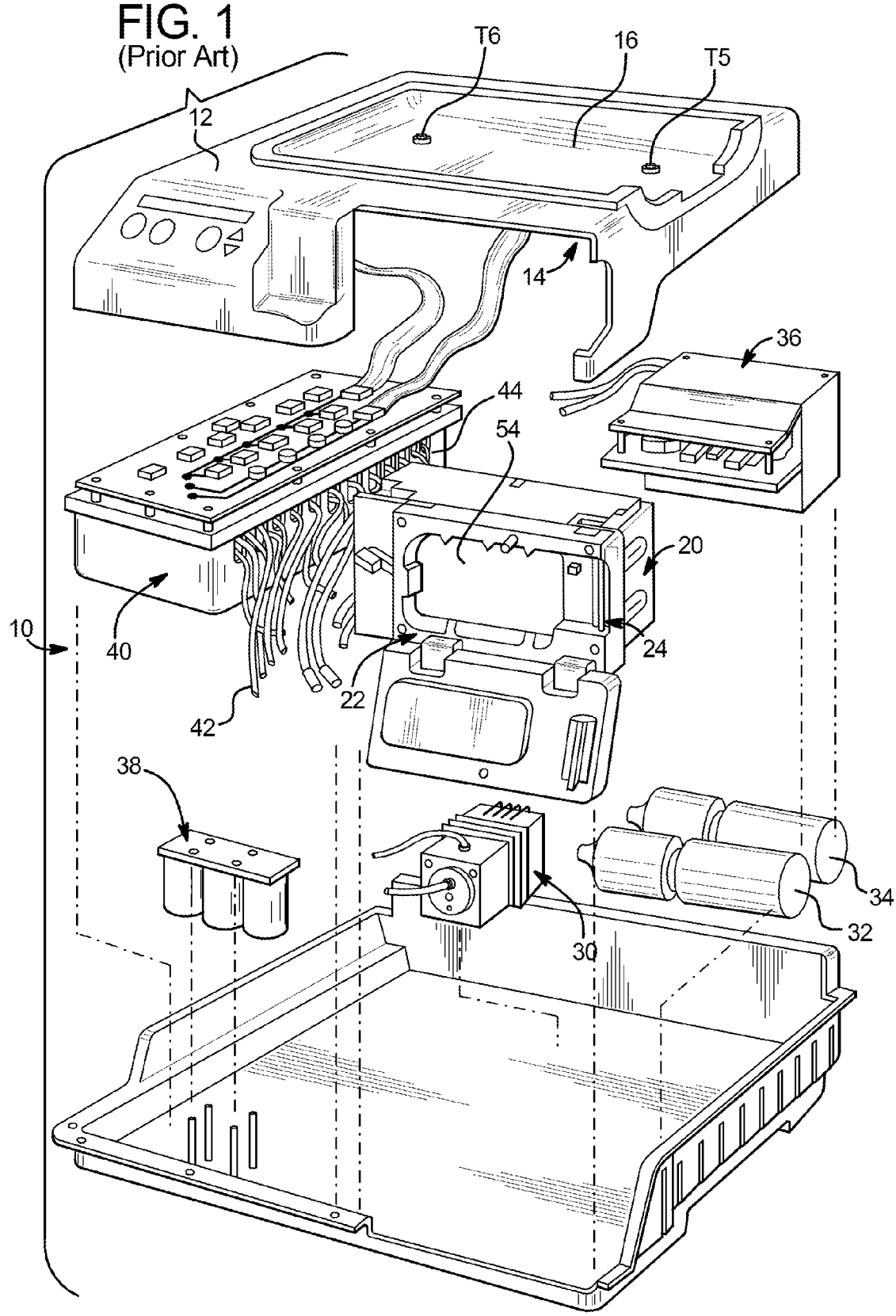
FIGS. 1 to 3 are various perspective views of a prior art peritoneal dialysis machine and in particular to a pneumatic system of the machine.

Referring now to the drawings and in particular to FIGS. 4 to 8, pressure manifold assembly 100 illustrates one embodiment of the present disclosure. Assembly 100 includes a top plate 102, a bottom valve plate 104 and a gasket 106 sandwiched between top plate 102 and bottom valve plate 104. Top plate 102 can be made of aluminum or other lightweight material that can be threaded or fitted with threaded inserts.

Manifold assembly 100 includes a first header 108, which is attached to manifold top plate 102 in a sealed manner using o-ring seals 110 and screws 112. 0-Ring seals 110 provide a leak tight connection between all of the internal passageways 134 (see FIG. 7) connecting first header 108 to manifold top plate 102. A plurality of hose barbs 114 on first header 108 connect the pneumatic passages of first header 108 to the pilot operated valves and pumps contained in actuator assembly (shown above in FIG. 1) using flexible urethane tubing (not shown) for example. The actuator assembly (shown above in FIG. 1) can be separated readily from manifold assembly 100 by removing screws 112.

Figure 2:
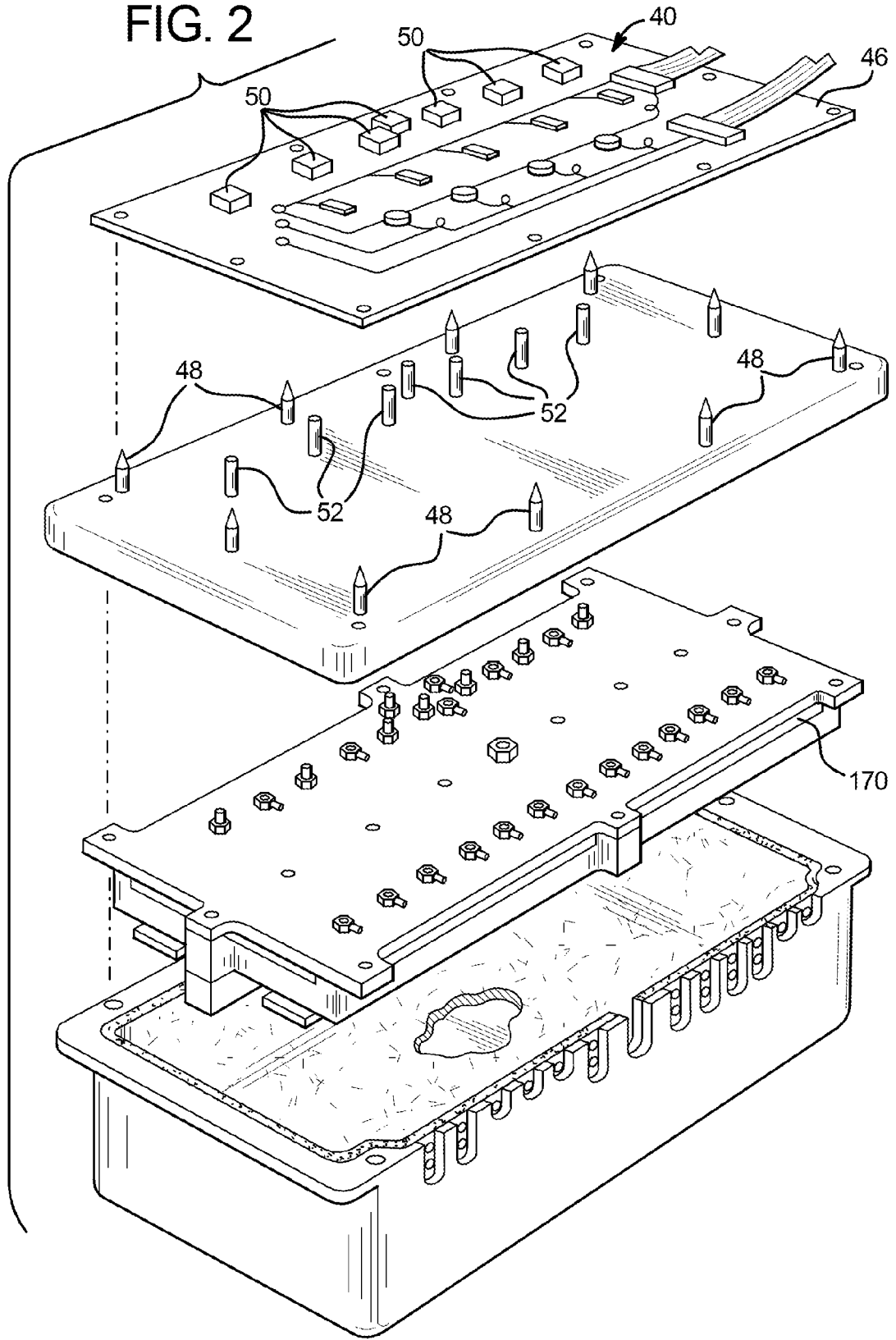

Manifold assembly 100 includes a second header 116, which is also attached to manifold top plate 102 in a sealed manner using o-ring seals 110 and screws 112. O-Ring seals 110 provide a leak tight connection between all of the internal passageways connecting second header 116 to manifold top plate 102. A plurality of hose barbs on second header 116 connect the pneumatic passages of second header 116 to pressure transducers contained in a separate printed circuit board assembly, which is similar to item 40 shown in FIG. 2 of the prior art using flexible urethane tubing (not shown). The pressure transducer printed circuit board 40 can be separated readily from manifold assembly 100 by removing screws 112 and is attached to header 116 via flexible, e.g., urethane, tubing only.

Figure 6:
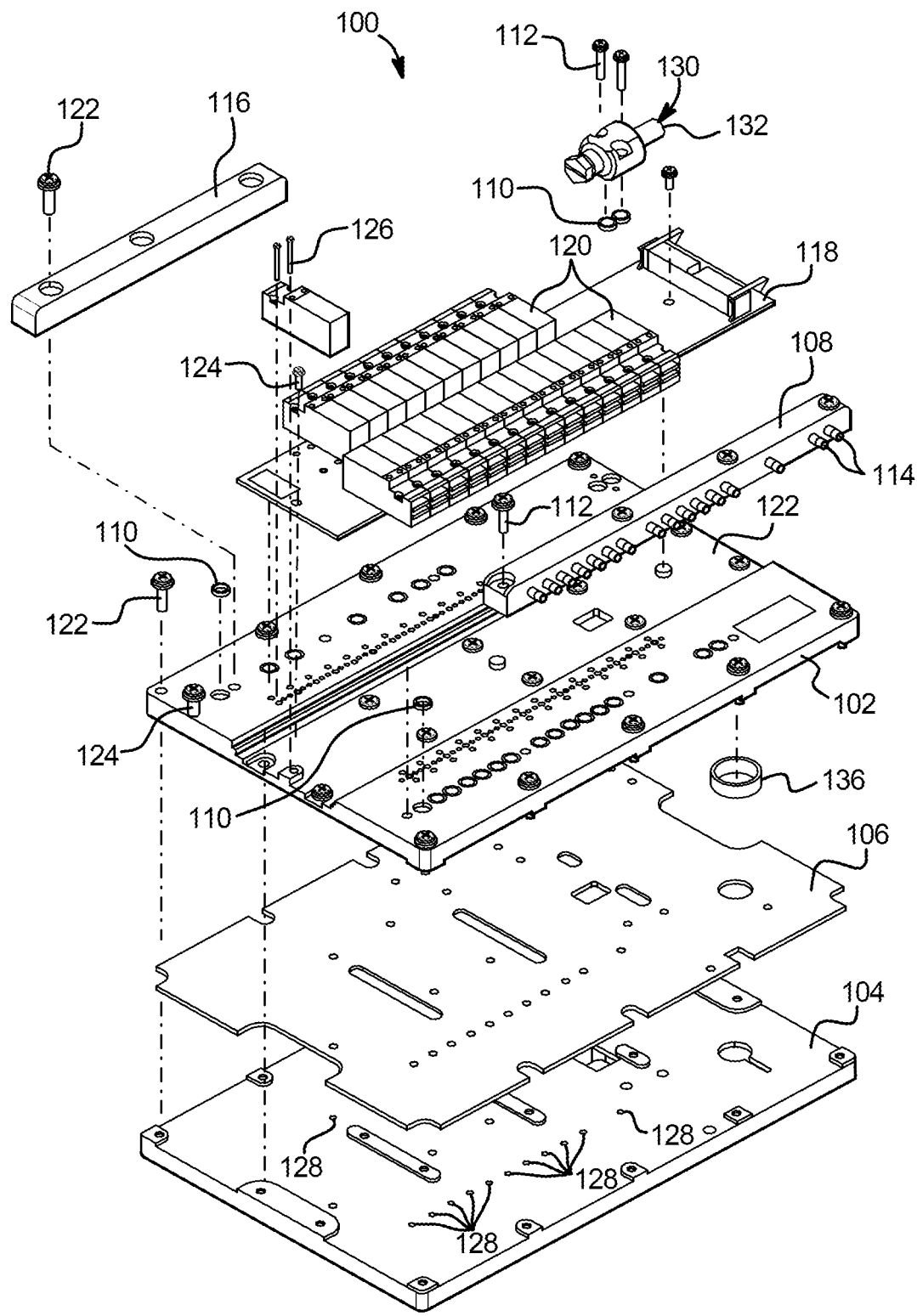
FIG. 6 illustrates one embodiment of a pressure manifold plate having pneumatic passageways, the plate operable with the pressure manifold assembly of the present disclosure.
Figure 7:
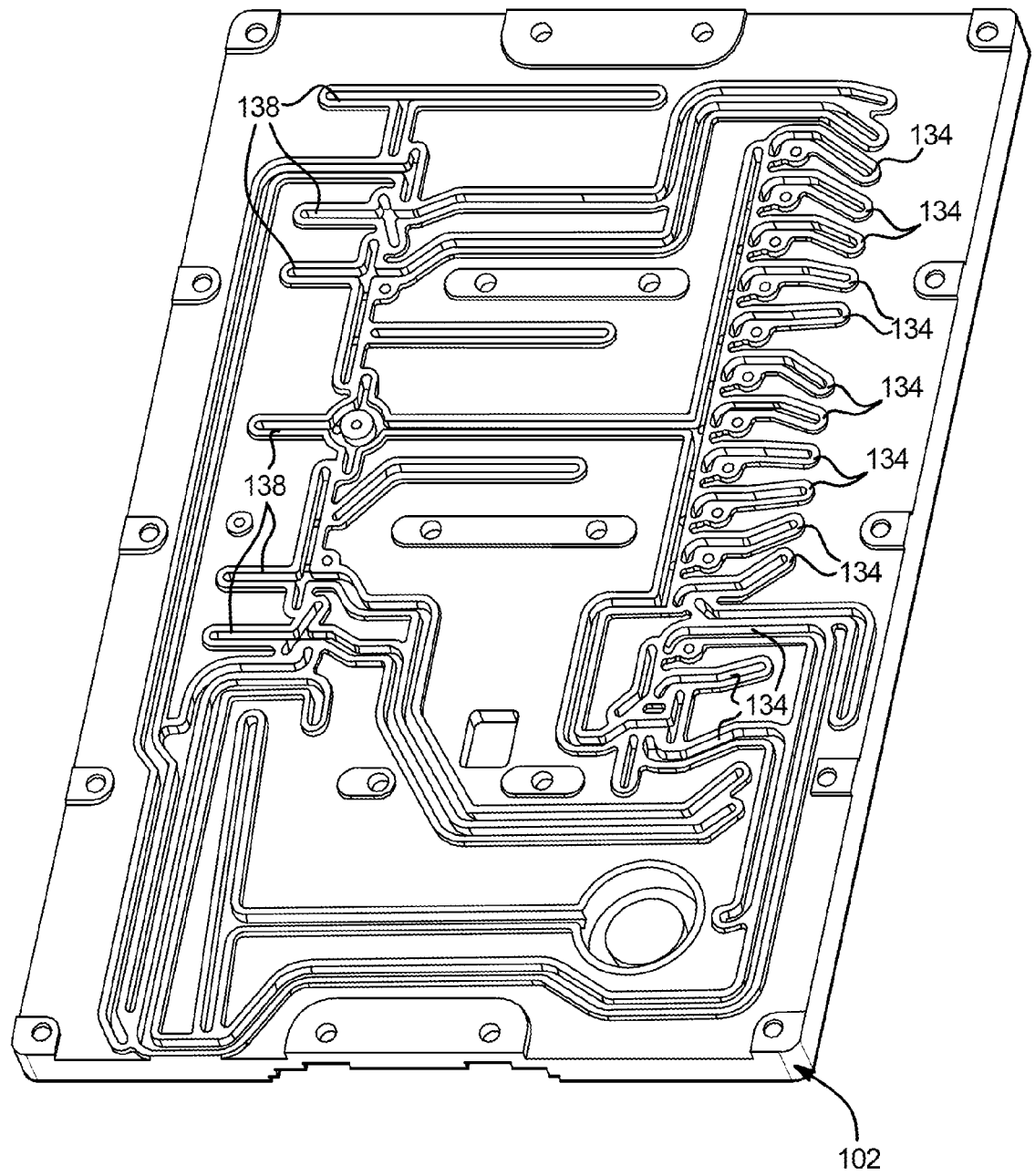
FIG. 7 is a perspective view of the underside of top plate 102 from the pressure manifold assembly of FIG. 4.

Referring now to FIG. 7, the underside of plate 102 (from that shown in FIGS. 4 and 6) is illustrated. Internal passageways 134, discussed above, pneumatically connect hose barbs 114 on first header 108 to ports of the right bank of valves 120 shown in FIG. 6. Likewise, internal passageways 138 pneumatically connect hose barbs 114 on second header 116 to the left bank of valves 120 in FIG. 6. Some of the other passageways in FIG. 7 are used to connect air pump heads 156 to filter 136, air tanks 140 and manual valve 130 as shown in schematics 200 and 210. There are also passageways in FIG. 7 that connect the right and left pump chambers (L_DISP and R_DISP), the right and left volumetric reference volumes (VSL and VSR), and their respective pressure sensors to the solenoid valves with which they communicate when pumping fluid and when measuring the volume of fluid that has been pumped.

Conversely, manifold assembly 100 can be removed from the machine by disconnecting headers 108 and 116 and removing an electrical connection to printed circuit board ("PCB") 118 from the PCB. PCB 118 controls valves 120.

PCB assembly 118 is placed in a recessed channel 122 in top plate 102 via shorter screws 124 before valves 120 are attached to top plate 102 via small screws 126. Electrical contact pins (not seen) extend down from valves 120 and plug into mating connectors (not seen) soldered to PCB assembly 118. Any of valves 120 can be removed easily and replaced by removing the two small screws 126.

Printed circuit board 118 contains a spike and hold circuit that energizes each of valves 120 with a twelve volt voltage spike and then reduces the applied voltage to a hold level to save energy and reduce the heat that valve 120 produces when it is held open. For example, the spike and hold circuit can reduce the supply voltage from twelve volts to 8.48 volts, which reduces the energy that needs to be dissipated (heat generated) up to fifty percent of that generated at twelve volts.

In an alternative embodiment, the spike and hold circuit is stored in software, e.g., via a memory and processor soldered to PCB 118. Here, smart power proportioning varies the spike duration depending upon how long it has been since the particular valve 120 has been actuated. For example, the processing and memory can set a spike duration for a valve 120 that has not been actuated recently to two-hundred milliseconds, and alternatively set a spike duration for a valve 120 that is continuously operated to only fifty milliseconds, further saving energy and reducing heat generation. The ability to vary the voltage profile that is applied to actuate solenoid valve 120 not only minimizes the heat that the valve generates (reducing the operating temperature of the valve), the variation also minimizes the amount of audible noise that valve 120 generates when energized. Reduced audible noise is especially advantageous when the dialysis machine is used at the patient's bedside, such as with a home peritoneal dialysis or home hemodialysis machine.

A diverter valve 130 is attached directly to top plate 102 via screws 112. Diverter valve 130 includes two ports on its underside, which seal to manifold 100 using o-rings 110 as shown in FIG. 6. Rotation of the slotted screw opposite an external port 132 of valve 130 connects the underside ports of valve 130 fluidly to port 132. External Port 132 in turn connects fluidly to an external pressure standard (not illustrated) for calibration of the pressure transducers. Rotating slotted screw to its original position blocks port 132, while enabling the two ports on the underside of diverter valve 130 to communicate fluidly.

A particulate filter 136 is sandwiched between top valve plate 102 and bottom valve plate 104. Gasket 106 seals top valve plate 102 to bottom valve plate 104 and to particulate filter 136.

Figure 5:
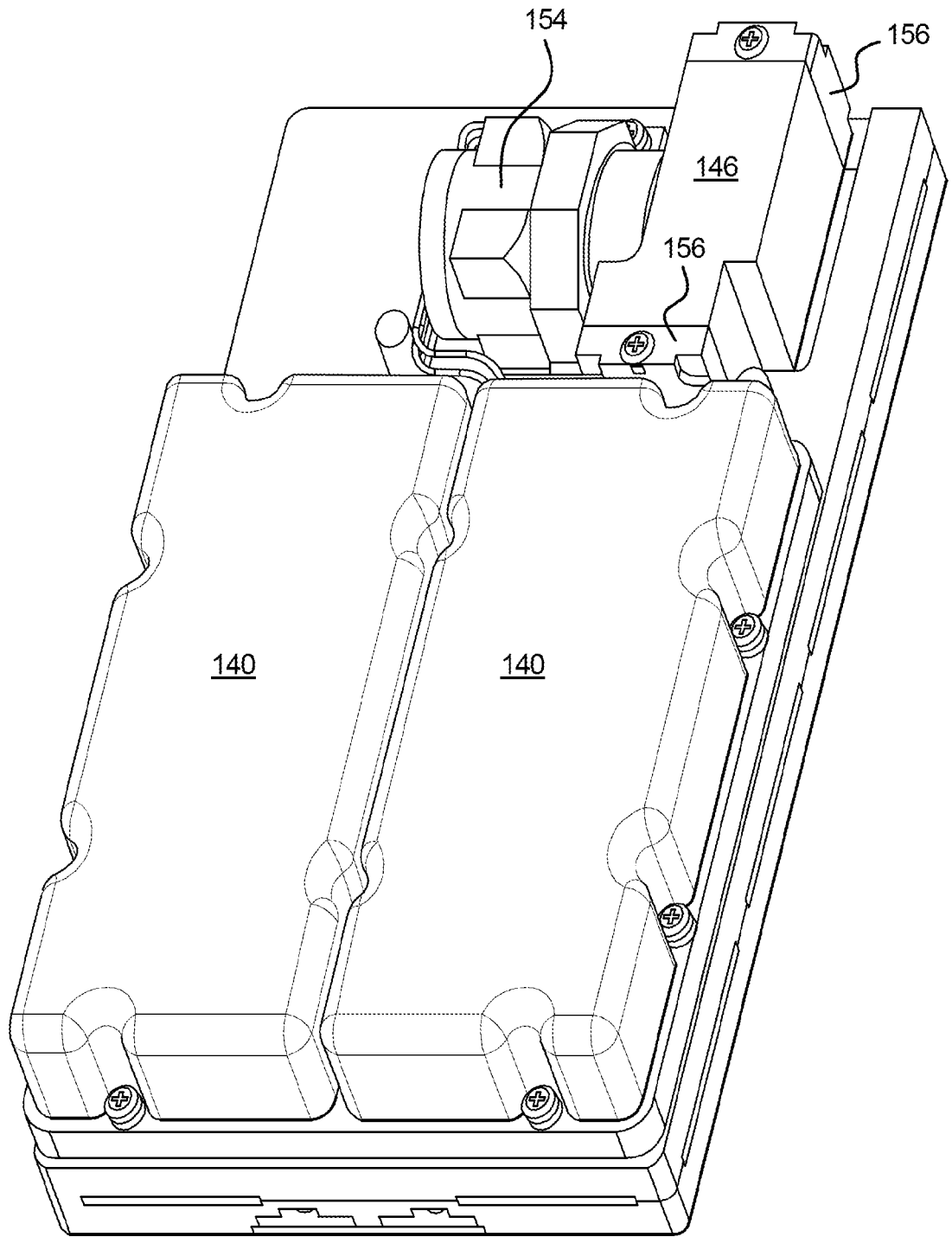
FIG. 5 is another perspective view of the pressure manifold assembly of FIG. 4.
Figure 8:
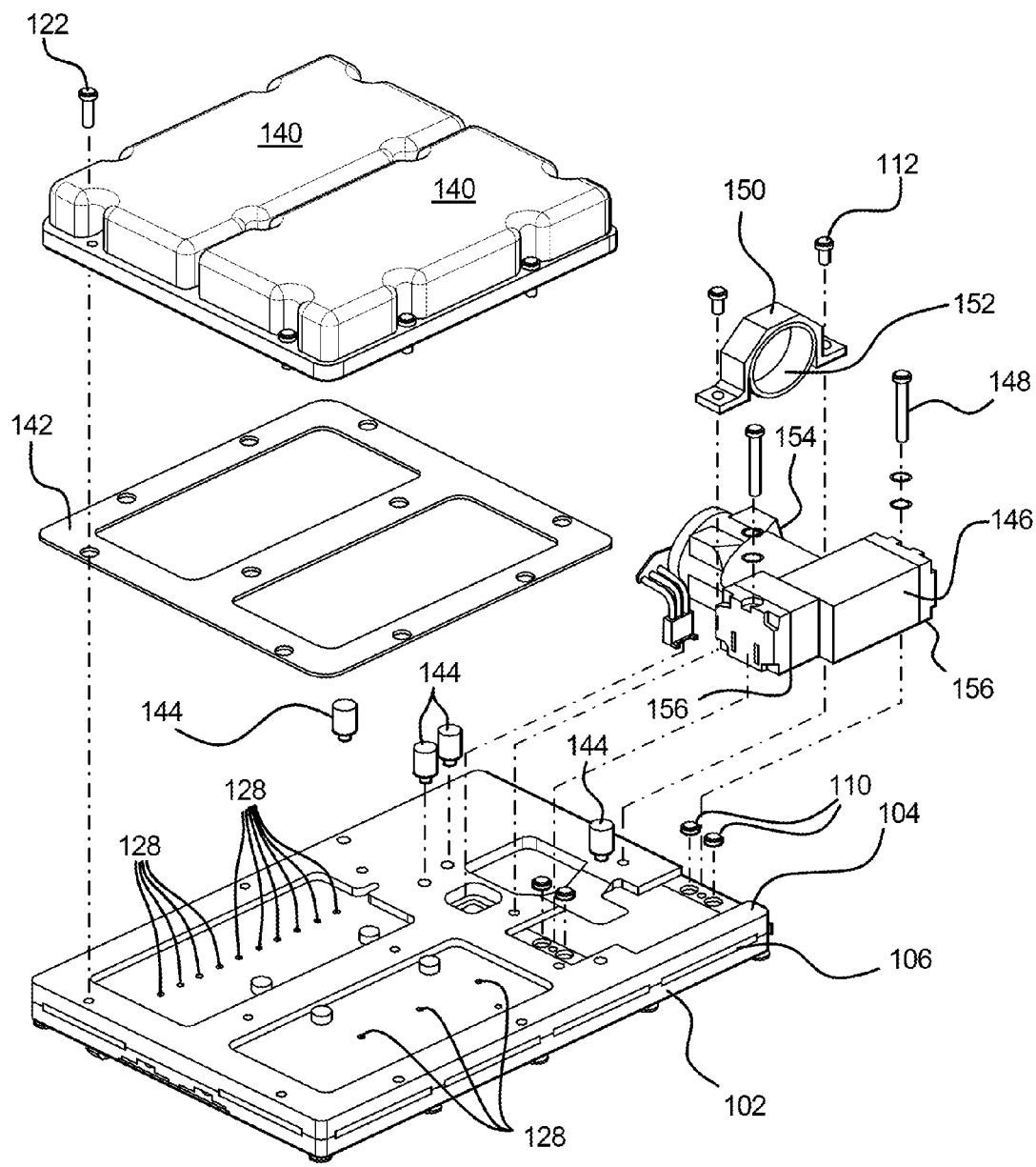
FIG. 8 is an exploded perspective view of a lower portion of the pressure manifold assembly of FIG. 4.

FIGS. 5 and 8 show molded, cast or machined pneumatic reservoirs 140 mounted to bottom plate 104 using screws 112. Pneumatic reservoirs 140 hold pressurized air for valves 120 to supply the pressurized air to different subsystems within the dialysis instrument. For example, valves 120 supply pressurized air to the fluid cassette valve chambers and pump chamber. Valves 120 also control air to seal the cassette for operation and to pressurize a bladder that retracts an occluder that otherwise is closed to clamp off all fluid lines for safety purposes. Pneumatic reservoirs 140 are shown below schematically in FIGS. 10 to 11.

The integrated pneumatic reservoirs 140 have multiple inlets and outlets in one embodiment, which are bores or holes 128 in plate 104 of manifold assembly 100 in one embodiment. As seen in FIGS. 6 through 8, the bores 128 run directly from one of the integrated reservoirs 140 to a valve 120, a pressure sensor, etc. One advantage of the direct connection is that the pressure sensor reads the actual pressure in the reservoir 140, not the pressure in a line connected to the reservoir, which can differ from the actual reservoir pressure when air is flowing into or from the reservoir 140.

Another advantage of communicating pneumatic reservoirs 140 of manifold assembly 100 with valves 120 via individual bores 128 is that if liquid is sucked into the manifold 100, e.g., in a situation in which sheeting on the disposable cassette has a hole located adjacent to one of the cassette's valves, liquid damage is mitigated. With assembly 100, fluid pulled into the assembly flows into one solenoid valve 120 only, after which the fluid discharged directly through a bore 128 associated with that valve 120 into Neg P Tank reservoir 140 without contaminating other valves 120 or other components. Thus, only a small portion of the pneumatic system might need replacing.

Gasket 142 seals pneumatic reservoirs 140 to bottom plate 104. Vent filters 144 minimize the sound produced when air enters (e.g., from POS T TANK or NEG P TANK as seen in FIGS. 10 and 11) and/or exits manifold assembly 100 and prevents particulate matter from entering manifold assembly 100 along with air.

Figure 10:
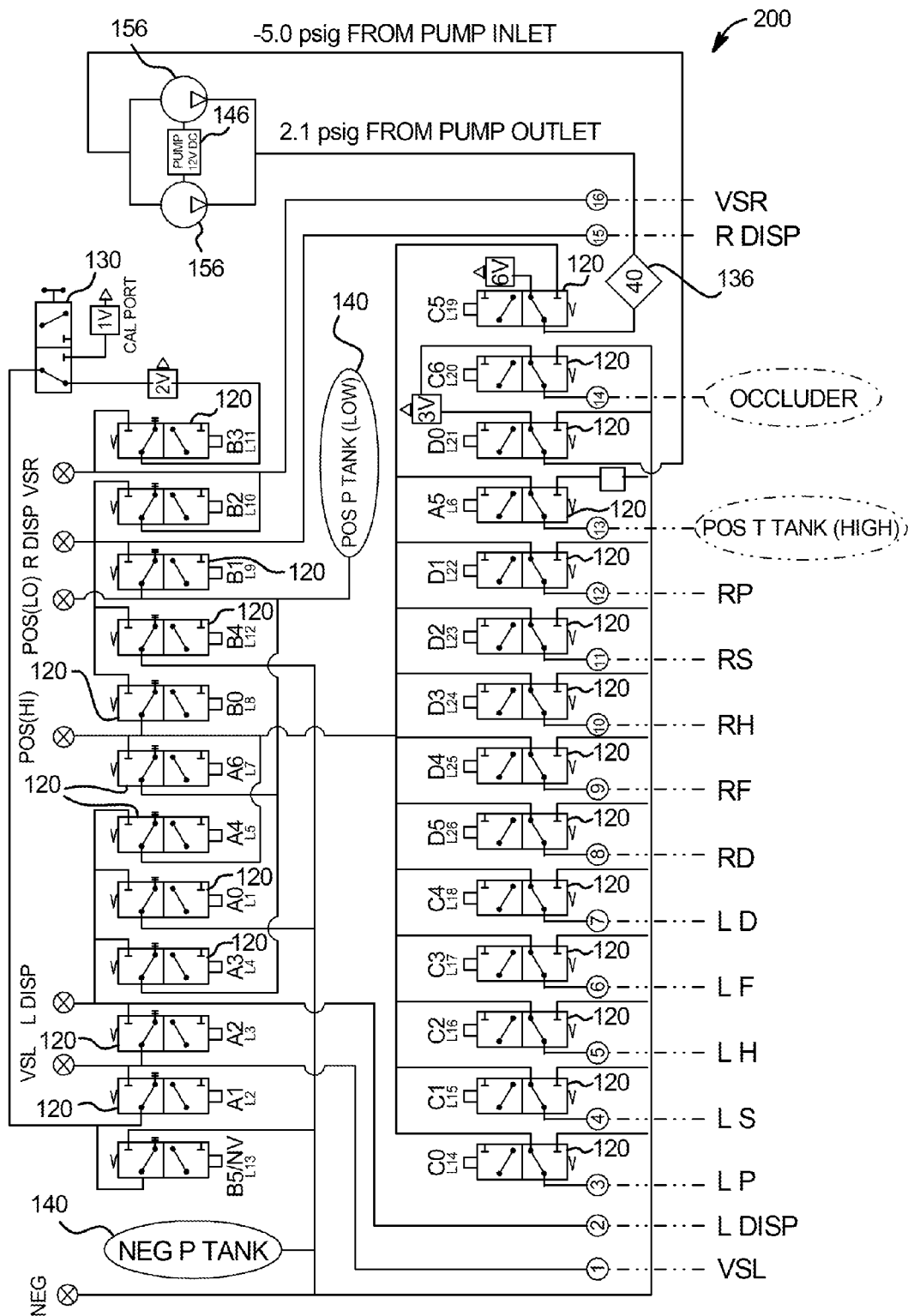
FIGS. 10 and 11 are schematic views of various pneumatic configurations for the pressure manifold assembly and other pneumatic components of the present disclosure.
Figure 11:
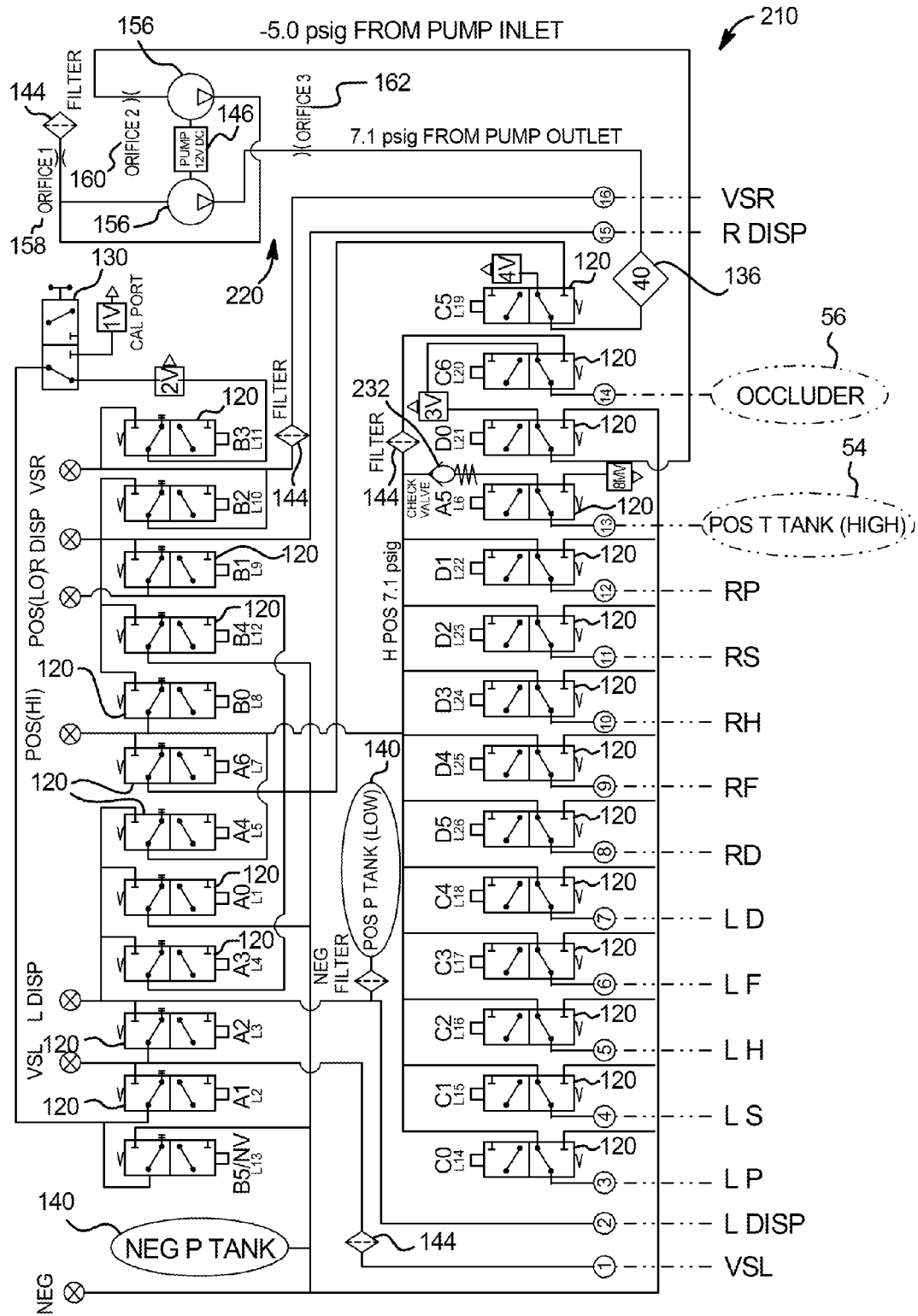

Manifold assembly 100 includes a pneumatic pump 146 marked as PUMP in FIGS. 10 and 11. Pneumatic pump 146 pressurizes pneumatic reservoirs 140 and the sealing bladders shown in FIGS. 10 and 11. The heads 156 of pump 146 are attached to bottom plate 104 using longer screws 148 on one end and clamp 150 and screws 112 on the other end. Electrometric seals (o-ring, quad-ring, quad-seal, etc.) 110 seal the pneumatic connection of the inlets and outlets of pump 146 to bottom plate 104. A thermally conductive pad 152 (e.g., Bergquist Gap Pad, Bergquist Sil Pad, Dow Corning TP 1500 or 2100, Fujipoly Sarcon, Laird T-Pli, T-Flex and T-Putty, or 3M 5507S) thermally links the motor 154 from pump 146 to bottom plate 104, so that bottom plate 104 becomes a heat sink for motor 154 and pump 146, absorbing the thermal energy that motor 154 creates. Bottom plate 104 is accordingly made of aluminum or other thermally conducting material in one embodiment. The thermal connection via thermally conductive pad 152 has been found to lower the operating temperature of pump motor 154 from around 100° C. to around 60° C., which should increase the life expectancy of pump 146.

The mounting and thermal coupling of pump 146 to bottom plate 104 also increases the effective mass of pump 146, so that pump 146 produces sound having a lower (and less bothersome) frequency and magnitude. Further, in one embodiment, manifold assembly 100 is mounted within a sealed (potentially air tight), acoustically insulated enclosure, further reducing magnitude of sound emanating from the enclosure. The lower operating temperature of pump 104 promotes use of the enclosure without over heating the manifold assembly.

Figure 9A:
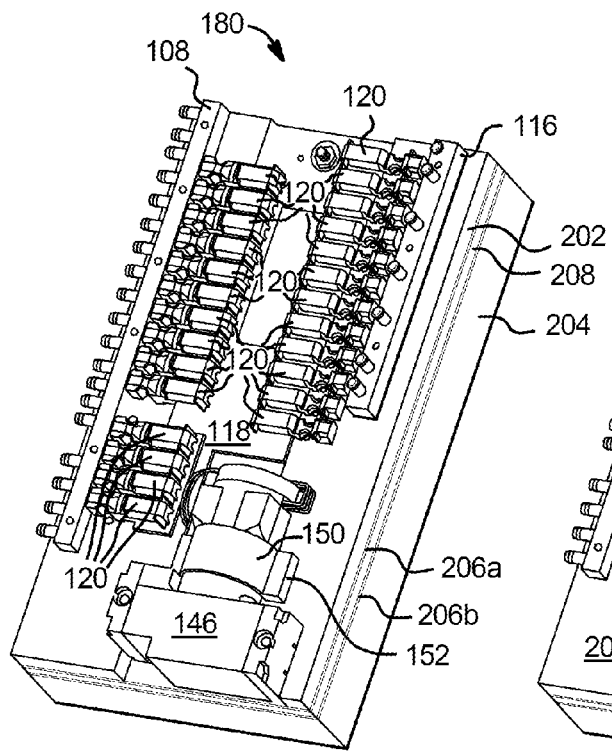
FIGS. 9A to 9D are perspective views of an alternative pressure manifold assembly of the present disclosure.

Referring now to FIGS. 9A to 9D, manifold assembly 180 illustrates one alternative manifold of the present disclosure. Here, pump 146 is located on the upper surface of the assembly with headers 108 and 116 and PCB 118. Mounting pump 146 as shown in FIG. 9A is advantageous because the pump is more accessible for servicing and because the manifold assembly is not as tall. Air reservoirs 140 located on the underside of manifold assembly 180 can be longer and do not need to have as much depth to achieve the same volume. The pump inlet and outlet ports of pump 146 can attach directly to the manifold using o-ring connections. Or, short lengths of flexible tubing can be bent in a u-shape and connect barbed ports located on the pump heads 156 of pump 146 to barbed fittings located on the underside of the plate upon which the pump heads 156 and pump 146 are mounted.

Locating pump 146 on the upper surface of the assembly allows only alternative upper plate 202 to be made of metal, e.g., aluminum. Alternative lower plate 204 and intermediate plate 208 can be made of plastic. Upper plate 202 is threaded to accept screws inserted through headers 108 and 116 and plates 204 and 208 to bolt those headers and plates to upper plate 202. Alternative gaskets 206a and 206b are located between intermediate plate 208 and upper and lower plates 202 and 204, respectively, to seal integral flow paths located on the insides of plates 202 and 204 (like paths 134 and 138 of FIG. 7) and around valve ports. Middle plate 208 separates gaskets 206a and 206b and provides a surface against which gaskets 206a and 206b can compress.

Figure 9B:
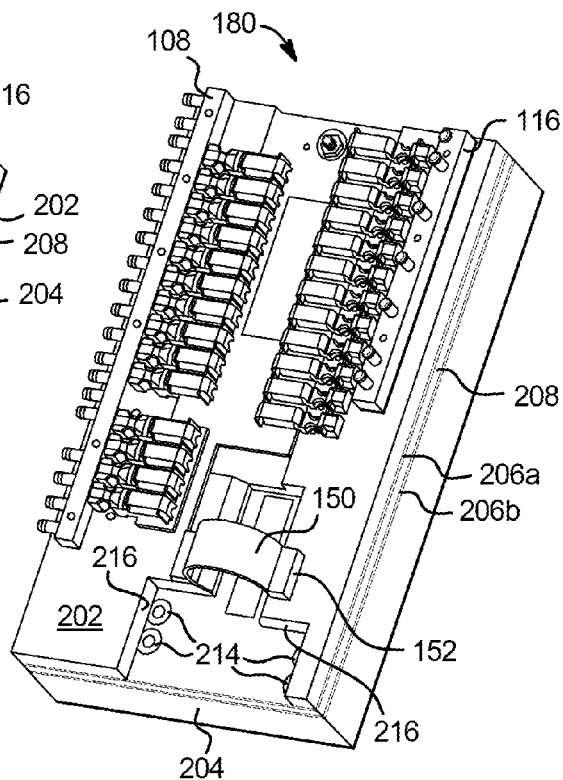

FIG. 9B shows pump 146 removed to illustrate that the pump mounts to elastomeric sealing inserts 214 placed in intermediate plate 208. FIGS. 9A and 9B illustrate that clamp 150 and conductive pad 152 connect to metallic upper plate 202 in the illustrated embodiment, so that the above-described heat sinking can occur. Upper plate 202 includes a recessed area 216 with a saddle that is designed for the heat sink mounting of pump 146 to upper plate 202.

Recessed area 216 forms or includes a saddle that pump motor 154 fits into. The saddle conducts the heat from pump motor 154 into upper plate 202, which is the only metallic plate as discussed in one embodiment. Top plate 202 includes all of the tapped holes for pump 146 and the other components of system 180. The outlet ports of heads 156 seal to middle plate 208, however, there is very little heat conducted from pump heads 156 to middle plate 208. Instead, air that is being pumped takes heat away from the pump heads 156 and so acts as a coolant.

Figure 9C:
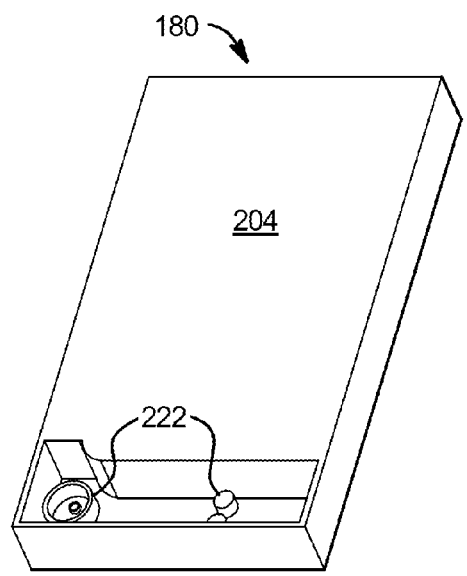
Figure 9D:
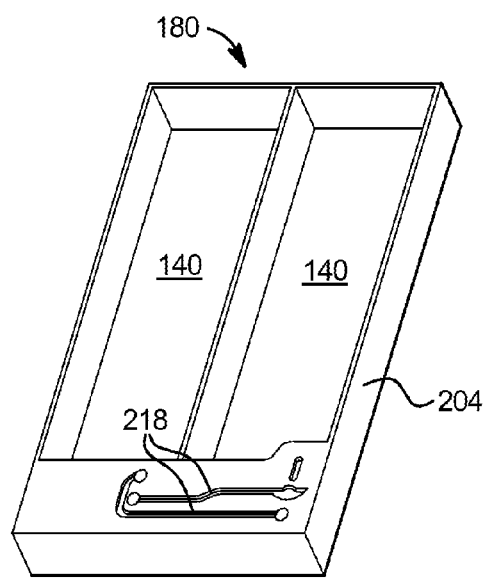

FIGS. 9C and 9D show different views of lower plate 204, which again is plastic in one embodiment. Lower plate includes molded pressure reservoirs 140 and flow paths 218. Features 222a and 222b on the underside of lower plate 204 accommodate filter 136 and elastomeric sealing inserts 214. Reservoirs 140, middle plate 208 and tubing headers 108 and 116 can all be molded plastic in one embodiment, reducing weight and cost.

Pneumatic System Configurations

Referring now to FIG. 10, schematic 200 illustrates one pneumatic schematic for manifold assembly 100 shown in FIGS. 4 to 8 and manifold assembly 180 of FIG. 9. FIG. 10 shows twelve valves on the left bank of valves, which correspond to the twelve valves 120 shown mounted on the left side of PCB 118 in FIGS. 4, 7 and 9. Likewise, the fourteen valves shown on the right bank of valves of schematic 200 correspond to the fourteen valves 120 shown on the right side of PCB 118 in FIGS. 4, 7 and 9. Schematic 200 of FIG. 10 includes a valve labeled B5/NV that is used to lower the vacuum level in negative pressure tank (NEG P Tank) 140 when fluid is to be drained from the patient instead of a supply bag. Previously, the equivalent of air pump 146 of FIG. 10 would be turned off and the equivalent of valve D0 (12) of FIG. 10 would be energized, so that air could bleed through air pump 146, lowering the vacuum level in Neg P Tank 140. The need for the vacuum pump to bleed through the pump severely limited the choice of air pumps that could be used because the vast majority of available air pumps do not allow a vacuum to be bled through the pump.

In schematic 200 of FIG. 10, pneumatic pump 146 includes two heads 156 (see also FIGS. 5 and 8) having inlets and outlets connected in parallel. Dual heads 156 individually pressurize reservoirs 140 simultaneously in the embodiment shown in schematic 210 of FIG. 11. One head is dedicated to pressurizing positive pressure reservoir (Pos P (Lo Pos) tank) 140. Positive pressure reservoir 140 in one embodiment is controlled at about 1.5 psig when pumping to the patient or at about 5.0 psig when pumping to a solution bag or drain line. The other head 156 is dedicated to evacuating negative pressure reservoir (Neg P tank) 140. Negative pressure reservoir 140 in one embodiment is controlled at about −1.5 psig when pumping from the patient or at about −5.0 psig when pumping from a solution bag. Because pump 146 does not have to switch back and forth between reservoirs 140, the reservoirs 140 are filled on a more constant and smooth basis, reducing noise and reducing the energy required to operate pump 146. Halving the flow to dual pump heads 156 reduces the pressure losses due to flow restrictions to nearly one-quarter of their original value. Running each reservoir at half flow rate reduces noise because the inrush of air to positive reservoir 140 or from negative reservoir 140 is less severe.

Both schematics 200 and 210 further include an inline filter 136 that prevents particulate generated at air pump 146 from entering manifold assembly 100 or 180. Schematics 200 and 210 also include a manually operated selector valve 130 (see FIGS. 4 and 6) for diverting a pathway in the manifold to an outside calibration port.

Pneumatic schematic 210 of FIG. 11 shows an alternative pneumatic configuration for manifold assemblies 100 and 180 of the present disclosure. Schematic 210 of FIG. 11 differs from schematic 200 of FIG. 10 in one respect because schematic 210 includes a three-way valve A6 that replaces a two-way Hi-Lo valve A6 of FIG. 11. Three-way valve A6 of system 10 allows air pump 146 to maintain the pressure in the Pos P (Lo Pos) tank 140 directly, while isolating an occluder tank 56 and Pos T (High Pos) tank (bladder 54 of FIG. 1).

The occluder tank 56 and Pos T tank 54 are in one embodiment bladders that can expand and contract with pressure changes. Bladder as used herein includes, without limitation, balloon type bladders and bellows type bladders. The force created by the Pos T bladder 54 seals a disposable cassette against a cassette holder 22 on machine 10 that operates one or more pump chamber and valve chamber located within the cassette. In one embodiment, pump 146 pressurizes both bladders 54 or 56 to about 7.1 psig. Previously, the bladder pressures have fluctuated between about 5 psig and 7.1 psig. The bladder pressures for schematic 210 of the present disclosure however have been narrowed to fluctuate between about 6.8 psig and about 7.1 psig. For schematic 200, the cassette sealing bladder pressure would normally fluctuate between 6.8 psig and 7.1 psig but can fall as low as five psig if the occluder is closed and re-opened. The system of schematic 210 eliminates the possibility of falling to five psig.

The force created by the occluder bladder 56 retracts an occluder bar by compressing plural coil springs, allowing fluid to flow to and from the cassette during normal operation. If occluder bladder 56 is not retracted, the occluder will extend, pinching the tubing lines that lead from the cassette to the patient, heater bag, supply bags and drain line so that fluid movement is prevented. Three-way valve A6 closes off cassette bladder 54 and occluder bladder 56 whenever the air pump has to pressurize Pos P Tank 140, so that no air is stolen from the bladder. For example, in one implementation, when machine 10 is pumping fluid to the patient, the Pos P (Low Pos) tank 140 pressure is maintained at 1.5 psig.

A replenishment of a heater bag (stored on tray 16 shown in FIG. 1) follows each patient fill, which requires five psig. To change pressure in Pos P tank 140 from 1.5 to five psig, PCB 118 energizes three-way valve A6, closing off the cassette sealing bladder and occluder bladder 56 supply lines so that the pressure in the bladders cannot fall. The pressure in the Pos T bladder 54 and occluder bladder 56 can momentarily fall to as low as about five psig at this time, which is close to the pressure needed to retract the occluder, i.e., the occluder could actuate inadvertently generating a creaking noise if the two-way valve of schematic 200 is used instead of the three-way isolating valve of schematic 210. In schematic 210, the pressure in the Pos T bladder 54 and occluder bladder 56 will not change upon a replenishment of the heater bag because pneumatic system 210 uses three-way valve A6.

In another example, if the pressure in Pos T bladder 54 falls to as low as about five psig, the seal between the disposable cassette and machine interface can be broken momentarily. It is possible that the seal will not be recreated when the pressure in Pos T bladder 54 is increased to its normal operating pressure of about 7.1 psi. Machine 10 without three-way valve A6 (e.g., schematic 200 of FIG. 10) can be configured to detect this leak by performing a pressure decay test on Pos T bladder 54 and post an alarm when such leak is detected. The alarm is cleared by cycling the power off and back on. If the pressure is below about 4.5 psig when the power comes back on, the therapy is terminated because the cassette seal is determined to have been broken. The machine operating according to schematic 210 however avoids this alarm by isolating Pos T bladder 54 from the pneumatic lines filling the occluder bladder 56 and/or the Pos P Tank 140, ensuring that Pos T bladder 54 is at the higher pressure.

Schematic 210 allows pump 146 to maintain the pressure in Pos P reservoir 140 directly, so that pump 146 only has to pump against either 1.5 or 5 psig. In schematic 200, Pos P reservoir 140 is maintained indirectly through Pos T bladder 54, which requires pump 146 to pump against 7.1 psig of Pos T bladder 54. Pump 146 generates less noise and less heat when it pumps against the lower pressure. Also, when the 7.1 psig Pos T bladder 54 and the occluder bladder 56 are connected to Pos P reservoir 140 by valve A6 in system 200, the 7.1 psig source produces a rush of air to the 1.5 psig destination. This rush of air generates a noticeable audible noise.

In another example, if the pressure of occluder bladder 56 falls to about 5 psig from 7.1 psig, the load on the compression springs decreases allowing the springs to extend the occluder partway but not enough to completely pinch-off the flow of fluid through the tubing leading to or from the cassette. The partial movement of the occluder results in an audible creaking noise that can wake up a sleeping patient. The isolation of three-way valve A6 prevents such partial occlusion from occurring.

Schematic 210 of FIG. 11 also arranges the dual heads 156 of pneumatic pump 146 so that one head is dedicated to positive pressure generation, while the other head is dedicated to negative pressure generation. The result is a lower rate of air flow through the system when the Pos T bladder 54, Pos P reservoir 140, Neg P reservoir 140 or occluder bladder 56 are being maintained, which generates less noise.

As seen additionally in FIG. 12, whenever the positive pressure of positive pump head 156 or the negative pressure of pump head 156 is not being used, the resulting air flows are diverted through a circuit 220 containing free-flow orifices 158, 160 and 162, operate as shown below. Free-flow orifices 160 and 162 create a resistance to airflow that maintains the sound produced by the air flow at a pitch that is very close to the sound that the pump produces when it is pressurizing the components of schematic 210. Although the "free flow" orifices 160 and 162 do not reduce the air flow or the sound, the orifices make the sound less offensive to the patient because the sound is maintained at the low pump frequency.

Figure 12:
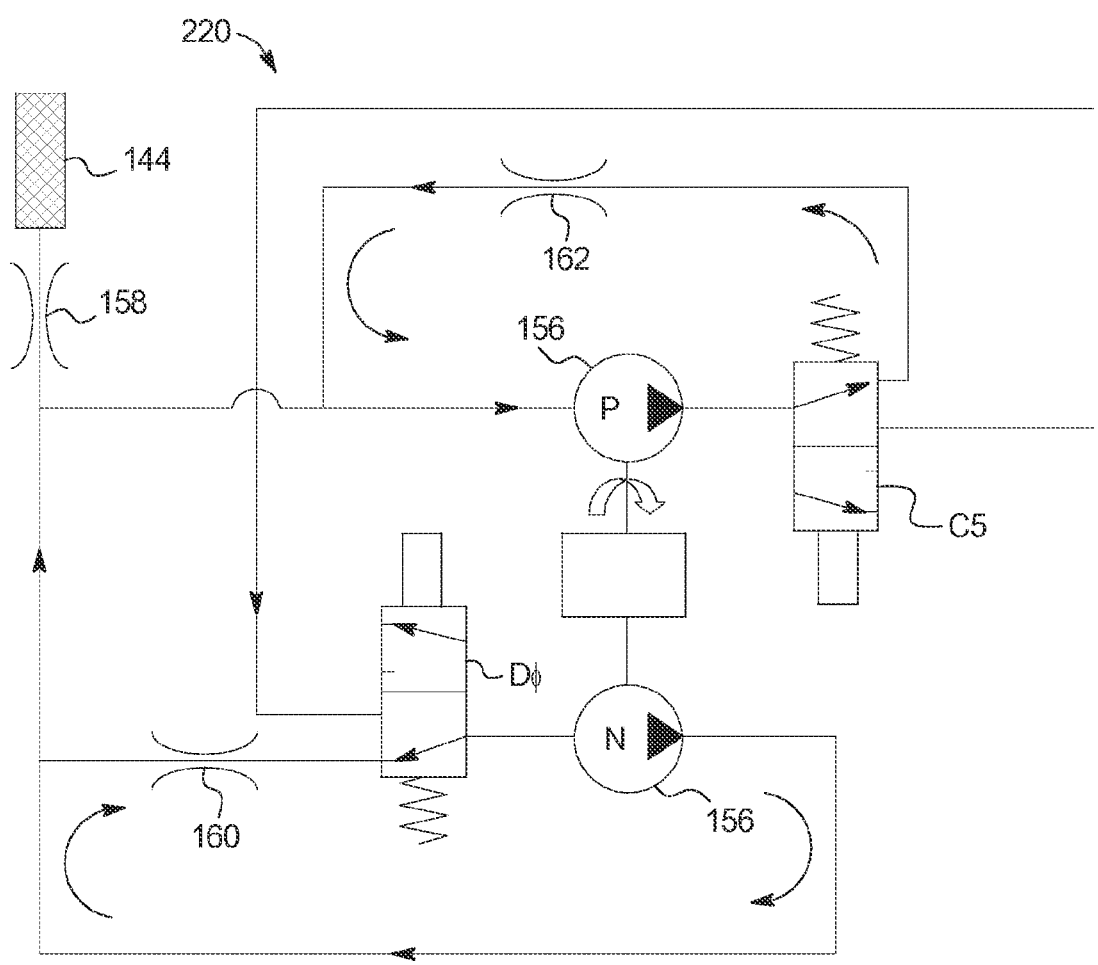
FIGS. 12 and 13 illustrate one embodiment of a noise reduction circuit operable with the pneumatic pump of the pressure manifold assemblies of the present disclosure.
Figure 13:
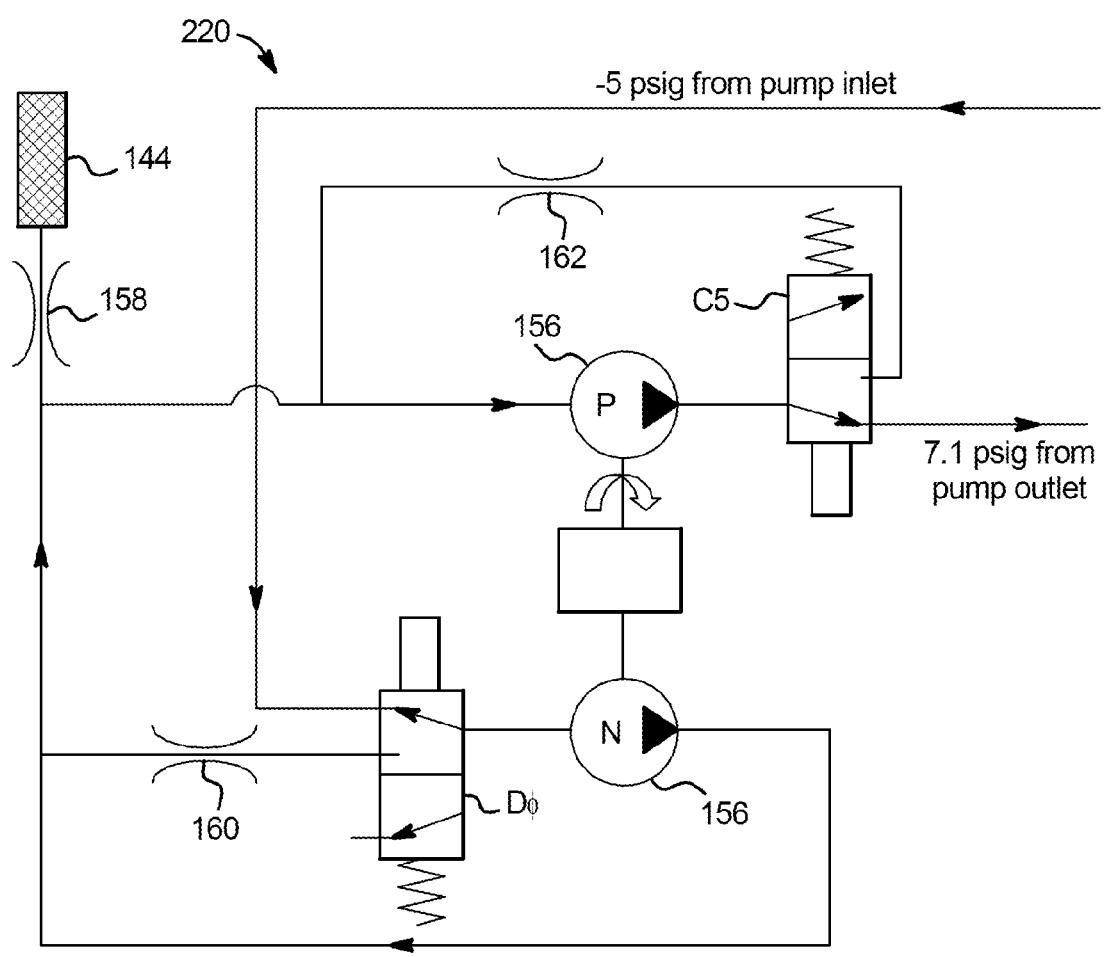

FIGS. 12 and 13 show noise reduction circuit 220 in two valve states. FIG. 12 is the de-energized, recirculation, noise reducing state. FIG. 13 is the energized, pressure-applying state. In FIG. 12, valves C5 and D0 (also seen in FIG. 11) are in the de-energized state. Each pump head 156 pumps in a recirculation loop with the outlet flow being directed back to the pump head inlet. Positive pressure orifice 162 and negative pressure orifice 160 maintain a partial load on positive pump head 156 and negative pump head 156, respectively.

When valves C5 and D0 switch state as shown in FIG. 13, the change in the load on the pump heads 156 is small, so that the pitch and amplitude difference between when pump 146 is running in (i) free flow (FIG. 12) and (ii) both pressure and vacuum (FIG. 13) is minimized Further, the change in the load on the negative pump head 156 is small, so that the pitch and amplitude difference between when pump 146 is running in (i) free flow (FIG. 12) and (iii) vacuum only (not shown but valve D0 is as in FIG. 13, while valve C5 is as in FIG. 12) is minimized. Still further, the change in the load on the negative pump head 156 is small, so that the pitch and amplitude difference between when pump 146 is running in (i) free flow (FIG. 12) and (iv) pressure only (not shown but valve D0 is as in FIG. 12, while valve C5 is as in FIG. 13) is minimized. It should also be appreciated that pitch and amplitude difference is minimized when switching from: state (ii) to state (i), (iii) or (iv); state (iii) to state (i), (ii) or (iv); and state (iv) to state (i), (ii) or (iii).

Figure 3:
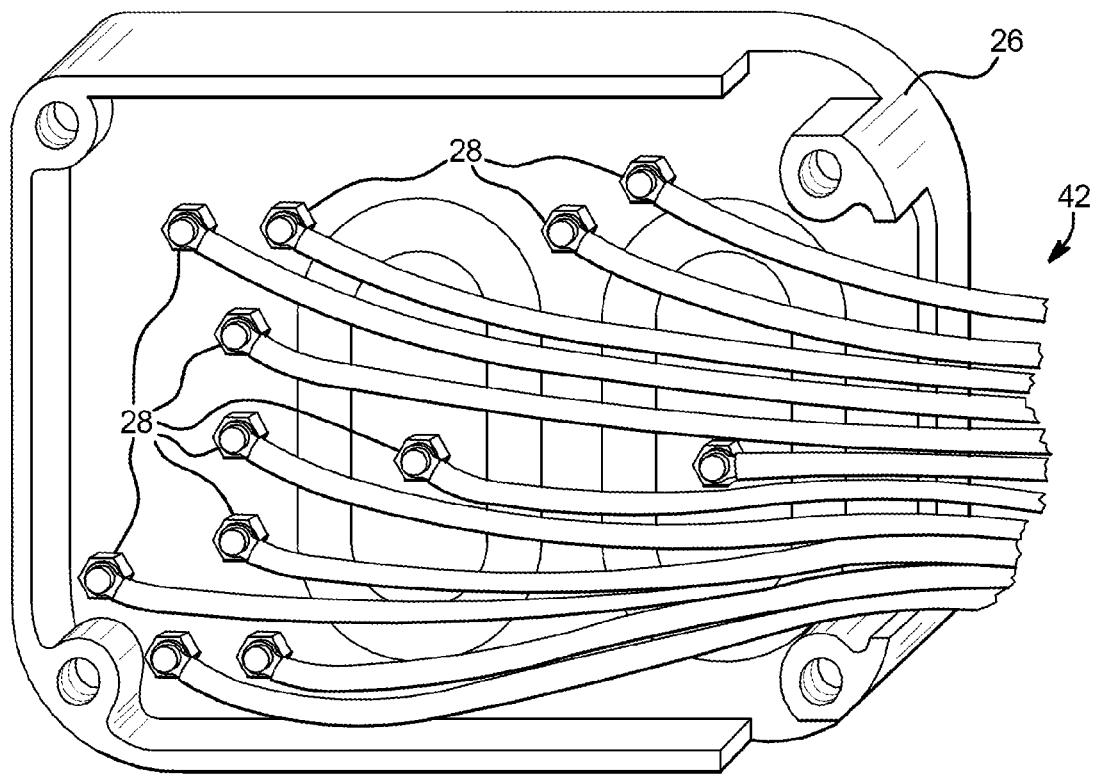
Figure 4:
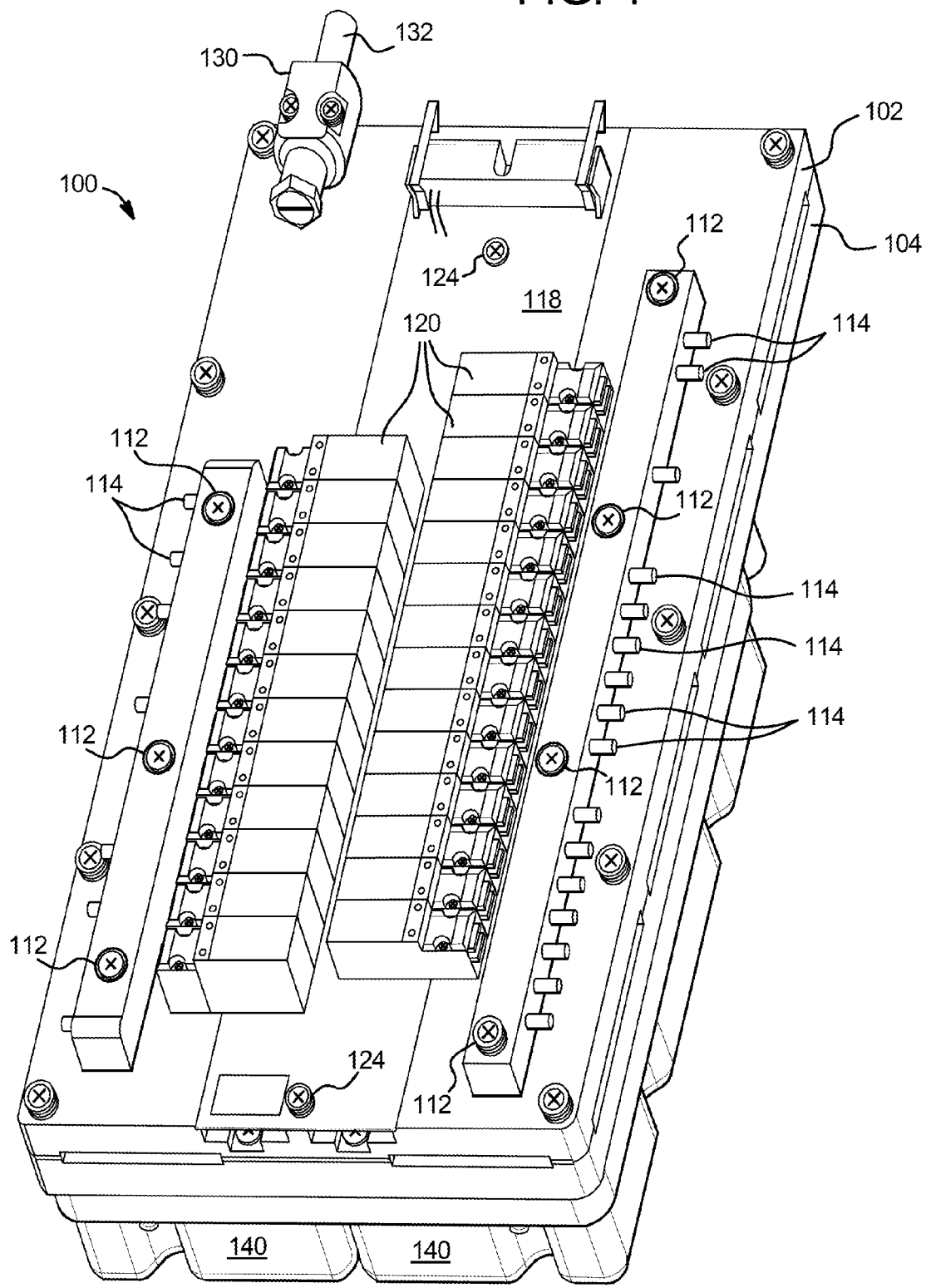
FIG. 4 is a perspective view of one embodiment of a pressure manifold assembly of the present disclosure.

Schematic 210 of FIG. 11 also includes plural filters 144 (FIG. 8) integrated into manifold assembly 100 in places that an inrush of flow can occur that could generate noise of a higher frequency and magnitude than a baseline noise. For example, one of the filters 144 reduces the magnitude of the noise that Pos P tank 54 generates when pressure is changed from 1.5 psig to 5 psig. Another filter 144 reduces the magnitude of the noise that is generated when the occluder bladder is pressurized. Still another pair of filters 144 reduces the magnitude of the noise that the connection of the pumping chambers 140 to the volumetric reference chambers located at cassette interface 26 (FIG. 3) creates during the fluid measurement process. Multi-layered manifold assembly 100 accommodates placement of the above filter elements 144 economically wherever they are needed.

Schematic 210 of FIG. 11 shows yet another improvement for integrated manifold assembly 100 or 180. A one-way flow check valve 212 is included in the conduit supplying pressure to the valve, which supplies PosT bladder 54, which in turn maintains the pressure that seals the cassette and its fluid pathways. Cassette-sealing bladder 54 with check valve 212 cannot lose pressure when or after occluder bladder 56 is pressurized. Check valve 212 thus prevents a loss of the seal between the cassette and gasket located in the cassette interface 26 due to a momentary loss of pressure of occluder bladder 56. A solenoid valve can be used instead of the one-way check valve.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A method of pneumatically operating a dialysis system comprising:
   (i) pumping air in a first valve state from a pneumatic pump to operate a component of the dialysis system; and
   (ii) recirculating air in a second valve state by pumping air from an outlet of the pneumatic pump to an inlet of the pneumatic pump to minimize at least one of a noise pitch or noise amplitude when switching from the second valve state to the first valve state.

2. The pneumatic method of claim 1, which includes reducing air flow in the second valve state.

3. The pneumatic method of claim 1, which includes filtering air supplied to the pneumatic pump.

4. The pneumatic method of claim 1, wherein pumping air includes pumping positive air pressure, and which includes locating a valve for producing the first and second valve states pneumatically downstream from the pneumatic pump.

5. The pneumatic method of claim 1, wherein pumping air includes pumping negative air pressure, and which includes locating a valve for producing the first and second valve states pneumatically upstream from the pneumatic pump.

6. The pneumatic method of claim 1, which includes energizing a first valve so as to produce the first valve state and de-energizing a second valve so as to produce the second valve state.

7. The pneumatic method of claim 1, which includes maintaining a partial load on the pneumatic pump in the second valve state.

8. A method of pneumatically operating a dialysis system comprising:
   (i) enabling air to be pulled in from a fluid flow portion of the dialysis system and to be selectively switched to instead be recirculated to reduce noise; and
   (ii) enabling air to be pushed out to the fluid flow portion of the dialysis system and to be selectively switched to instead be recirculated to reduce noise.

9. The pneumatic method of claim 8, wherein pulling air includes pulling air into a first pump head and pushing air includes pushing air out of a second pump head.

10. The pneumatic method of claim 8, wherein air in (i) is recirculated in a different loop than is air in (ii).

11. The pneumatic method of claim 8, wherein recirculating air in at least one of (i) and (ii) further includes restricting the flow of the air.

* * * * *